(12) United States Patent
Bergman et al.

(10) Patent No.: US 8,900,126 B2
(45) Date of Patent: *Dec. 2, 2014

(54) OPTICAL SCANNING DEVICE

(75) Inventors: Harris Bergman, Marietta, GA (US);
Scott Cahall, Fairport, NY (US);
Giorgos Hatzilias, Buford, GA (US);
Karol Hatzilias, Atlanta, GA (US);
David G. Stites, Saint Petersburg, FL (US)

(73) Assignee: United Sciences, LLC, Atlanta, GA (US)

( * ) Notice: Subject to any disclaimer, the term of this patent is extended or adjusted under 35 U.S.C. 154(b) by 384 days.

This patent is subject to a terminal disclaimer.

(21) Appl. No.: 13/417,767

(22) Filed: Mar. 12, 2012

(65) Prior Publication Data

US 2012/0281071 A1 Nov. 8, 2012

Related U.S. Application Data

(60) Provisional application No. 61/466,863, filed on Mar. 23, 2011.

(51) Int. Cl.
*A61B 1/04* (2006.01)
(Continued)

(52) U.S. Cl.
CPC ......... *G01B 11/25* (2013.01); *A61B 2019/5289* (2013.01); *A61B 5/1077* (2013.01);
(Continued)

(58) Field of Classification Search
CPC ........... A61B 1/00179; A61B 1/00172; A61B 1/227; A61B 1/00009; A61B 1/05; A61B 1/04; A61B 1/043; A61B 1/045; A61B 1/0676; A61B 1/00045; A61B 1/00052; A61B 1/0607; A61B 1/0615; A61B 1/0623; A61B 1/063; A61B 2019/5255; A61B 2019/5257; A61B 2019/5295; G02B 1/00
USPC ......... 600/103, 108, 109, 117, 118, 131, 160, 600/178–180, 182, 200; 356/603; 382/128
See application file for complete search history.

(56) References Cited

U.S. PATENT DOCUMENTS 4,185,918 A   1/1980   DiMatteo et al.
4,396,945 A   8/1983   DiMatteo et al.
(Continued)

FOREIGN PATENT DOCUMENTS

WO   WO 2010/140074 A1   12/2010
WO   WO 2012/129229 A2   9/2012
(Continued)

OTHER PUBLICATIONS

PCT Search Report and Written Opinion, May 9, 2013, PCT Application No. PCTUS2013028218, 7 pages.
(Continued)

*Primary Examiner* — Thomas J Sweet
*Assistant Examiner* — William Chou
(74) *Attorney, Agent, or Firm* — John R. Biggers; H. Artoush Ohanian; Biggers Kennedy Lenart Spraggins LLP

(57) ABSTRACT

A device for scanning a body orifice or surface including a light source and a wide angle lens. The light from the light source is projected in a pattern distal or adjacent to the wide angle lens. Preferably, the pattern is within a focal surface of the wide angle lens. The pattern intersects a surface of the body orifice, such as an ear canal, and defines a partial lateral portion of the pattern extending along the surface. A processor is configured to receive an image of the lateral portion from the wide angle lens and determine a position of the lateral portion in a coordinate system using a known focal surface of the wide angle lens. Multiple lateral portions are reconstructed by the processor to build a three-dimensional shape. This three-dimensional shape may be used for purposes such as diagnostic, navigation, or custom-fitting of medical devices, such as hearing aids.

30 Claims, 15 Drawing Sheets

(51) Int. Cl.

| | | |
|---|---|---|
| *A61B 1/06* | (2006.01) | |
| *A61B 1/00* | (2006.01) | |
| *A61B 5/107* | (2006.01) | |
| *G01B 11/25* | (2006.01) | |
| *H04N 5/232* | (2006.01) | |
| *A61B 19/00* | (2006.01) | |
| *H04N 5/225* | (2006.01) | |

(52) U.S. Cl.
 CPC . *A61B 2019/5255* (2013.01); *A61B 2019/5217* (2013.01); *H04N 5/23238* (2013.01); *A61B 5/1079* (2013.01); *H04N 2005/2255* (2013.01)
 USPC ........................... 600/109; 600/160; 600/117

(56) References Cited

U.S. PATENT DOCUMENTS

| | | | |
|---|---|---|---|
| 4,434,800 A | 3/1984 | Anson et al. | |
| 4,575,805 A | 3/1986 | Moermann et al. | |
| 4,585,349 A | 4/1986 | Gross et al. | |
| 4,622,967 A | 11/1986 | Schachar | |
| 4,637,715 A | 1/1987 | Idesawa | |
| 4,645,348 A | 2/1987 | Dewar et al. | |
| 4,705,401 A | 11/1987 | Addleman et al. | |
| 4,774,403 A | 9/1988 | Arts | |
| 4,821,117 A | 4/1989 | Sekiguchi | |
| 4,885,634 A | 12/1989 | Yabe | |
| 4,967,092 A | 10/1990 | Fraignier et al. | |
| 4,986,262 A | 1/1991 | Saito | |
| 5,044,373 A | 9/1991 | Northeved et al. | |
| 5,056,204 A | 10/1991 | Bartschi | |
| 5,090,400 A | 2/1992 | Saito | |
| 5,200,819 A | 4/1993 | Nudelman et al. | |
| 5,218,427 A | 6/1993 | Koch | |
| 5,280,378 A | 1/1994 | Lombardo | |
| 5,294,940 A | 3/1994 | Wennagel et al. | |
| 5,419,312 A | 5/1995 | Arenberg et al. | |
| 5,432,543 A | 7/1995 | Hasegawa et al. | |
| 5,436,655 A | 7/1995 | Hiyama et al. | |
| 5,487,012 A | 1/1996 | Topholm et al. | |
| 5,546,189 A | 8/1996 | Svetkoff et al. | |
| 5,605,531 A | 2/1997 | Lane et al. | |
| 5,658,235 A | 8/1997 | Priest et al. | |
| 5,702,249 A | 12/1997 | Cooper | |
| 5,714,832 A | 2/1998 | Shirrod et al. | |
| 5,733,246 A | 3/1998 | Forkey | |
| 5,738,633 A | 4/1998 | Christiansen | |
| 5,740,802 A | 4/1998 | Nafis et al. | |
| 5,747,789 A | 5/1998 | Godik | |
| 5,753,931 A | 5/1998 | Borchers et al. | |
| 5,784,098 A | 7/1998 | Shoji et al. | |
| 5,825,495 A | 10/1998 | Huber | |
| 5,831,601 A | 11/1998 | Vogeley et al. | |
| 5,840,017 A | 11/1998 | Furusawa et al. | |
| 5,847,832 A | 12/1998 | Liskow et al. | |
| 5,883,385 A | 3/1999 | Takahashi et al. | |
| 5,891,016 A | 4/1999 | Utsui et al. | |
| 5,895,927 A | 4/1999 | Brown | |
| 5,897,494 A | 4/1999 | Flock et al. | |
| 5,926,388 A | 7/1999 | Kimbrough et al. | |
| 5,936,628 A | 8/1999 | Kitamura et al. | |
| 5,978,092 A | 11/1999 | Brown | |
| 6,028,672 A | 2/2000 | Geng | |
| 6,044,170 A | 3/2000 | Migdal et al. | |
| 6,069,698 A | 5/2000 | Ozawa et al. | |
| 6,081,612 A | 6/2000 | Gutkowicz-Krusin et al. | |
| 6,110,106 A | 8/2000 | MacKinnon et al. | |
| 6,179,777 B1 | 1/2001 | Ninomiya et al. | |
| 6,186,944 B1 | 2/2001 | Tsai | |
| 6,217,510 B1 | 4/2001 | Ozawa et al. | |
| 6,292,263 B1 | 9/2001 | Norita et al. | |
| 6,293,911 B1 | 9/2001 | Imaizumi et al. | |
| 6,319,199 B1 | 11/2001 | Sheehan et al. | |
| 6,327,041 B1 | 12/2001 | Guern | |
| 6,361,489 B1 | 3/2002 | Tsai | |
| 6,377,865 B1 | 4/2002 | Edelsbrunner et al. | |
| 6,383,133 B1 | 5/2002 | Jones | |
| 6,393,431 B1 | 5/2002 | Salvati et al. | |
| 6,450,970 B1 | 9/2002 | Mahler et al. | |
| 6,459,493 B1 | 10/2002 | Sugiura et al. | |
| 6,470,124 B1 | 10/2002 | Le Gargasson et al. | |
| 6,471,636 B1 | 10/2002 | Sano et al. | |
| 6,532,299 B1 | 3/2003 | Sachdeva et al. | |
| 6,573,513 B2 | 6/2003 | Hayashi | |
| 6,602,186 B1 | 8/2003 | Sugimoto et al. | |
| 6,603,552 B2 | 8/2003 | Cline et al. | |
| 6,626,825 B2 | 9/2003 | Tsai | |
| 6,675,040 B1 | 1/2004 | Cosman | |
| 6,679,839 B2 | 1/2004 | Farkas et al. | |
| 6,751,494 B2 | 6/2004 | Collier et al. | |
| 6,753,966 B2 | 6/2004 | Von Rosenberg | |
| 6,918,538 B2 | 7/2005 | Breytman et al. | |
| 6,920,414 B2 | 7/2005 | Tøpholm | |
| 6,937,348 B2 | 8/2005 | Geng | |
| 6,949,069 B2 | 9/2005 | Farkas et al. | |
| 7,068,825 B2 * | 6/2006 | Rubbert et al. | ................ 382/128 |
| 7,110,124 B2 | 9/2006 | Jensen et al. | |
| 7,137,948 B2 | 11/2006 | Tsai | |
| 7,162,323 B2 | 1/2007 | Brumback et al. | |
| 7,179,222 B2 | 2/2007 | Imaizumi et al. | |
| 7,206,067 B2 | 4/2007 | Jensen et al. | |
| 7,251,025 B2 | 7/2007 | Jensen et al. | |
| 7,258,663 B2 | 8/2007 | Doguchi et al. | |
| 7,311,723 B2 | 12/2007 | Seibel et al. | |
| 7,341,557 B2 | 3/2008 | Cline et al. | |
| 7,371,218 B2 | 5/2008 | Walston et al. | |
| 7,399,181 B2 | 7/2008 | Weber et al. | |
| 7,419,467 B2 | 9/2008 | Tsai | |
| 7,421,140 B2 | 9/2008 | Rottem | |
| 7,440,121 B2 | 10/2008 | Stone | |
| 7,446,885 B2 | 11/2008 | Zabolitzky et al. | |
| 7,448,753 B1 | 11/2008 | Chinnock | |
| 7,490,085 B2 | 2/2009 | Walker et al. | |
| 7,544,163 B2 | 6/2009 | MacKinnon et al. | |
| 7,553,020 B2 | 6/2009 | Goldfain et al. | |
| 7,583,872 B2 | 9/2009 | Seibel et al. | |
| 7,625,335 B2 | 12/2009 | Deichmann et al. | |
| 7,722,534 B2 | 5/2010 | Cline et al. | |
| 7,742,635 B2 | 6/2010 | Rohaly et al. | |
| 7,801,584 B2 | 9/2010 | Iddan et al. | |
| 7,802,909 B2 | 9/2010 | Baker | |
| 7,813,591 B2 | 10/2010 | Paley et al. | |
| 7,835,925 B2 | 11/2010 | Roe et al. | |
| 7,912,257 B2 | 3/2011 | Paley et al. | |
| 7,925,333 B2 | 4/2011 | Weir et al. | |
| 7,937,253 B2 | 5/2011 | Anast et al. | |
| 7,949,385 B2 | 5/2011 | Khamene et al. | |
| 7,955,255 B2 | 6/2011 | Boulais et al. | |
| 7,961,981 B2 | 6/2011 | Berg | |
| 7,976,474 B2 | 7/2011 | Zoth et al. | |
| 7,995,214 B2 | 8/2011 | Forster et al. | |
| 7,996,068 B2 | 8/2011 | Telischak et al. | |
| 8,035,637 B2 | 10/2011 | Kriveshko | |
| 8,100,826 B2 | 1/2012 | Mackinnon et al. | |
| 8,107,086 B2 | 1/2012 | Hart et al. | |
| 8,112,146 B2 | 2/2012 | Hart et al. | |
| 8,169,470 B2 | 5/2012 | Ishihara et al. | |
| 8,206,290 B2 | 6/2012 | Huang | |
| 8,212,884 B2 | 7/2012 | Seibel et al. | |
| 8,228,368 B2 | 7/2012 | Zhao et al. | |
| 8,239,001 B2 | 8/2012 | Verard et al. | |
| 8,249,461 B2 | 8/2012 | Vaerndal | |
| 8,271,069 B2 | 9/2012 | Jascob et al. | |
| 8,310,560 B2 | 11/2012 | Hart et al. | |
| 8,319,184 B2 | 11/2012 | Hart et al. | |
| 8,328,731 B2 | 12/2012 | Hessel et al. | |
| 8,384,916 B2 | 2/2013 | Hart et al. | |
| 2001/0044668 A1 | 11/2001 | Kimbrough et al. | |
| 2001/0051766 A1 | 12/2001 | Gazdzinski | |
| 2001/0055462 A1 * | 12/2001 | Seibel | .................. 385/147 |
| 2002/0161282 A1 | 10/2002 | Fulghum | |
| 2003/0074174 A1 | 4/2003 | Fu et al. | |
| 2003/0139658 A1 | 7/2003 | Collier et al. | |
| 2003/0139673 A1 | 7/2003 | Vivenzio et al. | |

(56) References Cited

U.S. PATENT DOCUMENTS

| | | | |
|---|---|---|---|
| 2003/0164952 A1* | 9/2003 | Deichmann et al. | 356/603 |
| 2003/0171655 A1 | 9/2003 | Newman et al. | |
| 2003/0210812 A1* | 11/2003 | Khamene et al. | 382/128 |
| 2004/0107080 A1 | 6/2004 | Deichmann et al. | |
| 2004/0122787 A1 | 6/2004 | Avinash et al. | |
| 2004/0136010 A1 | 7/2004 | Jensen et al. | |
| 2005/0068544 A1 | 3/2005 | Doemens et al. | |
| 2006/0133634 A1 | 6/2006 | Berg | |
| 2006/0282009 A1 | 12/2006 | Oberg et al. | |
| 2007/0035707 A1 | 2/2007 | Margulis | |
| 2007/0112273 A1 | 5/2007 | Rogers | |
| 2007/0153296 A1 | 7/2007 | Schick | |
| 2007/0156021 A1* | 7/2007 | Morse et al. | 600/167 |
| 2007/0237306 A1 | 10/2007 | Jones et al. | |
| 2007/0270647 A1 | 11/2007 | Nahen et al. | |
| 2007/0270788 A1 | 11/2007 | Nahen et al. | |
| 2008/0045799 A1 | 2/2008 | Whitehead et al. | |
| 2008/0045800 A2 | 2/2008 | Farr | |
| 2008/0058629 A1 | 3/2008 | Seibel et al. | |
| 2008/0081950 A1* | 4/2008 | Koenig et al. | 600/160 |
| 2008/0119693 A1 | 5/2008 | Makower et al. | |
| 2008/0146915 A1 | 6/2008 | McMorrow | |
| 2008/0208006 A1 | 8/2008 | Farr | |
| 2008/0208297 A1 | 8/2008 | Gertner et al. | |
| 2008/0275483 A1 | 11/2008 | Makower et al. | |
| 2008/0281156 A1 | 11/2008 | Makower et al. | |
| 2008/0281167 A1 | 11/2008 | Soderberg et al. | |
| 2009/0018465 A1 | 1/2009 | Hessel et al. | |
| 2009/0021818 A1* | 1/2009 | Weir et al. | 359/224 |
| 2009/0028407 A1 | 1/2009 | Seibel et al. | |
| 2009/0189972 A1 | 7/2009 | Harris et al. | |
| 2009/0221880 A1 | 9/2009 | Soderberg et al. | |
| 2009/0221920 A1 | 9/2009 | Boppart et al. | |
| 2009/0292168 A1 | 11/2009 | Farr | |
| 2009/0312638 A1 | 12/2009 | Bartlett | |
| 2009/0318758 A1 | 12/2009 | Farr et al. | |
| 2010/0020333 A1 | 1/2010 | Kunz et al. | |
| 2010/0060718 A1 | 3/2010 | Forster et al. | |
| 2010/0191144 A1 | 7/2010 | Zoth et al. | |
| 2010/0198009 A1 | 8/2010 | Farr et al. | |
| 2010/0231513 A1 | 9/2010 | Deliwala | |
| 2010/0239126 A1 | 9/2010 | Grafenberg et al. | |
| 2010/0296664 A1 | 11/2010 | Burgett et al. | |
| 2011/0009694 A1* | 1/2011 | Schultz et al. | 600/109 |
| 2011/0026037 A1 | 2/2011 | Forster et al. | |
| 2011/0028790 A1 | 2/2011 | Farr et al. | |
| 2011/0102763 A1 | 5/2011 | Brown et al. | |
| 2011/0130652 A1 | 6/2011 | Boppart et al. | |
| 2011/0137118 A1 | 6/2011 | Huang | |
| 2012/0039493 A1 | 2/2012 | Rucker et al. | |
| 2012/0057734 A1 | 3/2012 | Ambrose et al. | |
| 2012/0063644 A1* | 3/2012 | Popovic | 382/103 |
| 2012/0140301 A1 | 6/2012 | Xu et al. | |
| 2012/0187190 A1 | 7/2012 | Wang et al. | |
| 2012/0191078 A1* | 7/2012 | Yadlowsky et al. | 606/10 |
| 2012/0281071 A1 | 11/2012 | Bergman et al. | |
| 2012/0310098 A1 | 12/2012 | Popovic | |
| 2012/0327287 A1 | 12/2012 | Meyers et al. | |
| 2012/0327426 A1 | 12/2012 | Hart et al. | |
| 2012/0327427 A1 | 12/2012 | Hart et al. | |
| 2013/0002426 A1 | 1/2013 | Hart et al. | |
| 2013/0002824 A1 | 1/2013 | Hart et al. | |
| 2013/0003078 A1 | 1/2013 | Hart et al. | |
| 2013/0027515 A1 | 1/2013 | Vinther et al. | |
| 2013/0027516 A1 | 1/2013 | Hart et al. | |
| 2013/0237754 A1 | 1/2013 | Berglund et al. | |
| 2013/0237758 A1 | 1/2013 | Berglund et al. | |
| 2013/0237756 A1 | 9/2013 | Berglund et al. | |
| 2013/0237757 A1 | 9/2013 | Berglund et al. | |
| 2013/0237759 A1 | 9/2013 | Berglund et al. | |
| 2013/0237764 A1 | 9/2013 | Berglund et al. | |
| 2014/0031680 A1 | 1/2014 | Berglund et al. | |
| 2014/0031701 A1 | 1/2014 | Berglund et al. | |
| 2014/0128743 A1 | 5/2014 | Yew et al. | |

FOREIGN PATENT DOCUMENTS

| | | |
|---|---|---|
| WO | WO 2013/138074 A2 | 9/2013 |
| WO | WO 2013/138077 A2 | 9/2013 |
| WO | WO 2013/138078 A2 | 9/2013 |
| WO | WO 2013/138079 A2 | 9/2013 |
| WO | WO 2013/138081 A1 | 9/2013 |
| WO | WO 2013/138082 A2 | 9/2013 |

OTHER PUBLICATIONS

PCT Search Report and Written Opinion, Apr. 26, 2013, PCT Application No. PCTUS2013028311, 9 pages.
PCT Search Report and Written Opinion, Apr. 26, 2013, PCT Application No. PCTUS2013028323, 9 pages.
PCT Search Report and Written Opinion, May 13, 2013, PCT Application No. PCTUS2013028364, 7 pages.
PCT Search Report and Written Opinion, May 10, 2013, PCT Application No. PCTUS2013028299, 11pages.
PCT Search Report and Written Opinion, May 3, 2013, PCT Application No. PCTUS2013028347, 9 pages.
PCT Search Report and Written Opinion, Jun. 7, 2012, PCT Application No. PCTUS2012029806, 13 pages.
Office Action, U.S. Appl. No. 13/417,649 Oct. 7, 2013 pp. 1-25.
Office Action, U.S. Appl. No. 13/586,411 Aug. 29, 2013, pp. 1-21.
Notice of Allowance, U.S. Appl. No. 13/586,411, Jan. 30, 2014, pp. 1-21.
Office Action U.S. Appl. No. 13/586,471 Oct. 7, 2013 pp. 1-23.
Office Action, U.S. Appl. No. 13/586,448 Oct. 8, 2013 pp. 1-24.
Office Action, U.S. Appl. No. 13/586,474 Oct. 9, 2013 pp. 1-24.
Office Action, U.S. Appl. No. 13/586,459 Oct. 7, 2013 pp. 1-25.
Final Office Action, U.S. Appl. No. 13/417,649 Jun. 18, 2014, pp. 1-17.

* cited by examiner

OPTICAL SCANNING DEVICE

CROSS-REFERENCE TO RELATED APPLICATION

This patent application claims the benefit and priority of U.S. Provisional Patent Application No. 61/466,863, filed Mar. 23, 2011, and entitled "Optical Scanning Device."

BACKGROUND

The present invention relates to determine the shape of surfaces of soft tissue, and more specifically, to determining such shapes using optical technology.

Hearing aids, hearing protection, and custom head phones often require silicone impressions to be made of a patient's ear canal. Audiologists pour the silicone material into an ear, wait for it to harden then manufacturers use the resulting silicone impression to create a custom fitting in-ear device. The process is slow, expensive, inconsistent, and unpleasant for the patient, and can even be dangerous.

Also, there are a range of other medical needs that benefit from determining the shape of body surfaces, including surfaces defining body orifices, such as the size of shape of an ear canal, throat, mouth, or nostrils of a patient. For example, surgery may be guided by knowing such shapes or medical devices fashioned to have a custom fit for such shapes.

There is a need, therefore, for improvements in the determination of body surface shapes, including the shapes and sizes of surfaces associated with body orifices.

SUMMARY

According to one embodiment of the present invention, a device for scanning a body orifice of a body includes a light source and a wide angle lens wherein the light from the light source is projected in a pattern distal to the wide angle lens.

In another embodiment, an embodiment of the present invention includes a method of determining geometry of a body orifice. The method includes projecting, with a light source, a pattern of light to a location in a coordinate system. At least a partial lateral portion of the pattern of light illuminates a surface of the body orifice. A position of the lateral portion in the coordinate system is determined using a camera with a focal surface, wherein the focal surface includes the location.

DETAILED DESCRIPTION OF EXAMPLE EMBODIMENTS

Figure 1:
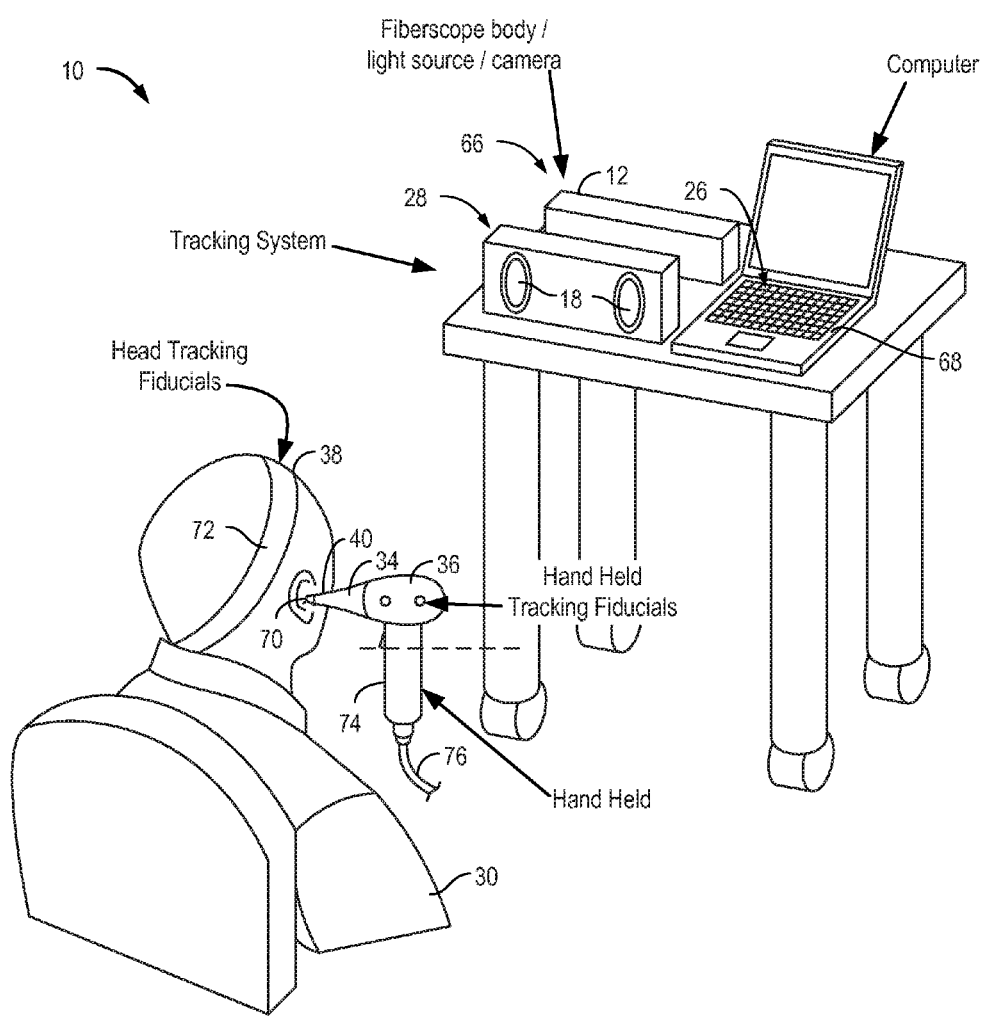
FIG. 1 is a schematic of a device of one embodiment of the present invention.

With reference now to FIGS. 1-4, embodiments of the present invention include a device 10 for scanning a body orifice or surface including a light source 12 and a wide angle lens 14. The light from the light source is projected in a pattern 16 distal or adjacent to the wide angle lens 14. Preferably, the pattern 16 is within a focal surface 18 of the wide angle lens 14. The pattern 16 intersects a surface of the body orifice, such as an ear canal, and defines a partial lateral portion 20 of the pattern extending along the surface. A processor 26 is configured to receive an image of the lateral portion 20 from the wide angle lens 14 and determine a position of the lateral portion in a coordinate system using a known focal surface of the wide angle lens 14.

The term "known" as used herein refers to known approximately within normal tolerances fit to achieve the desired resolution. Thus, the known focal surface has some thickness and variation to it that corresponds to the result of normal manufacturing tolerances.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Referring again to FIGS. 1 and 2, a body 30 of the patient being examined with the device 10. The device may further include a handheld probe 34, an optical hardware assembly 66, a tracking system 28 and a computer 68.

Notably, some or all of the elements of the optical hardware assembly 66, including the light sources for the laser and/or the fiberscope, the tracking system 28 and the computer 68 can be contained within the body of the handheld probe 34.

The body 30 of the patient defines any of a plurality of orifices or body surfaces that can be investigated by embodiments of the present invention for medical purposes. Body markers 38 or fiducials adorn the portion of the body 30 defining the surface or orifice of interest. For example, a head band 72 extends around the head near the ear canal 70 and supports a plurality of retro-reflective spheres.

It should also be noted that non-medical uses are possible, such as measuring of tortuous openings or surfaces in an industrial setting. However, embodiments of the present invention are particularly well-suited to measure surfaces of an ear canal 70 which has a small diameter (approximately 6 mm). The ear canal optionally has and at least one bend along its length.

The probe 34 includes a handle 74, a cable 76, a probe shaft 40, and a plurality of probe markers 38. The cable 76 includes a light conductor 42 and a plurality of image conductors 44 and connects the probe 34 to the optical hardware assembly 66. The image conductors may conduct the optical images, such as through a fiber optic line, or through communicating an electrical signal containing the image data. The term "conductor" therefore is used in its broadest sense herein to include conducting of any signal, analog or digital, power or information or data. A conductor may also represent wireless communication such as by an RF signal.

The optical hardware assembly includes a fiberscope body, the light source 12 and a camera. The fiberscope body is connected via one of the image conductors 44 to the probe 34. The camera is connected to the fiberscope body and receives images therefrom for navigation of the probe 34 within the body orifice. Similarly, the light source, in this case a laser light source, connects to the probe 34 via the light conductor 42.

The tracking system 28 includes a pair of cameras 78 spaced apart and pointed toward the probe markers 36 and the body marker 38. Optionally, there are at least three probe markers. The tracking system 28 may be an integrated system that is configured to track and report the position of objects within its coordinate system, or one marker relative to another, using on-board hardware and software. Or, the processing functions may be distributed, such as within the computer system 68 of the embodiment illustrated in FIG. 1.

The computer system 68 is connected to the optical hardware assembly 66 and the tracking system 28. Within the computer is the processor 26 and additional components described in more detail in FIG. 13. Generally, the computer system is configured to receive data from the probe 34, including data on the lateral portions 20 of the light pattern 16 intersecting surfaces of the body orifice, and data from the tracking system 28, including position data of the probe 34 and the wearer's body relative to a coordinate system. And, the computer's processor 26 is configured to use the data to determine a three-dimensional shape of the body surfaces, such as the shape of the ear canal 70, for use in building customized hearing aids.

Figure 2:
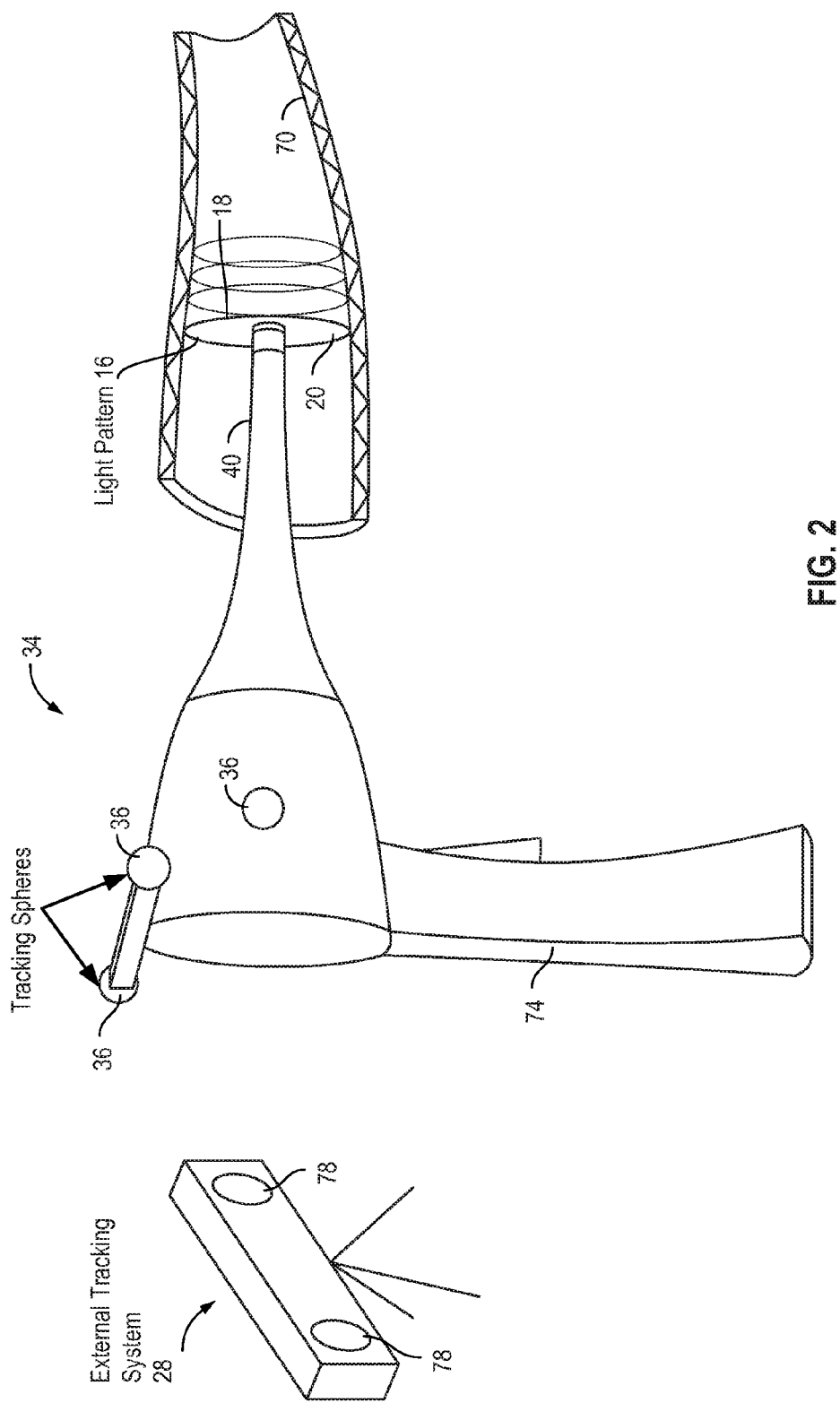
FIG. 2 is a schematic of a probe of another embodiment of the present invention.

Referring to FIG. 2, the probe 34 is shown in greater schematic detail and includes the probe markers 36 in the form of a plurality of retro-reflective tracking spheres within the field of view of the cameras 78 of the tracking system 28. As described above, optionally, three or more probe markers 36 are used and the probe comprises three or more such probe markers. Generally, absent other assumptions or information, three spheres are the minimum needed to lock down all 6 degrees of freedom. Emitting from a distal end of the probe is the light pattern 16 (in this case a planar surface, but it could also be a cone of light, or a beam or some other surface shape) extending through the transparent side walls 58 of a cap 56 and forming one or more lateral portions 20 as it intersects the inner surfaces of the ear canal 70. The probe 34 is advantageously sized to move within the ear canal 70 to capture several shapes that are communicated to the computer system 68 for assembly into the three-dimensional shape 32.

FIGS. 3A, 3B, 3C, 3D, and 3F are even more detailed views of the distal end of the probe 34. The probe can optionally comprise one or more of the light conductor 42, the image conductors 44, the cap 56, a reflector 48, a mask 50, a cone mirror 52 and a fiber scope 54.

Figure 3A:
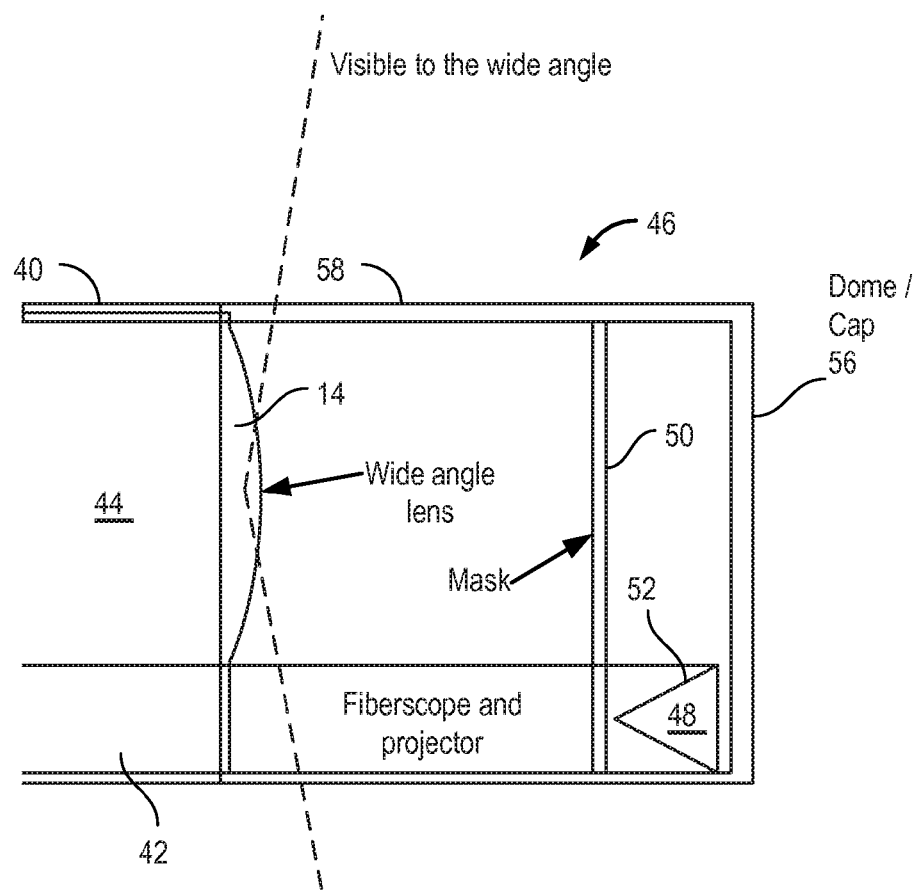
FIGS. 3A-3E are various views of a distal tip of the probe of FIG. 2.
Figure 3B:
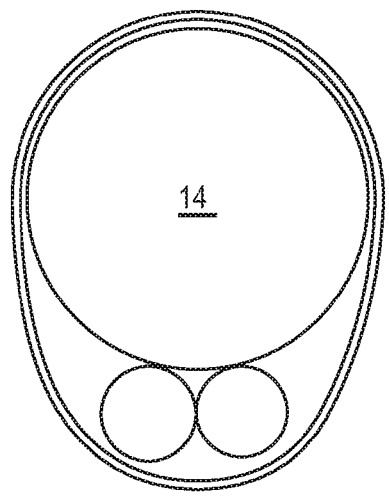
Figure 3C:
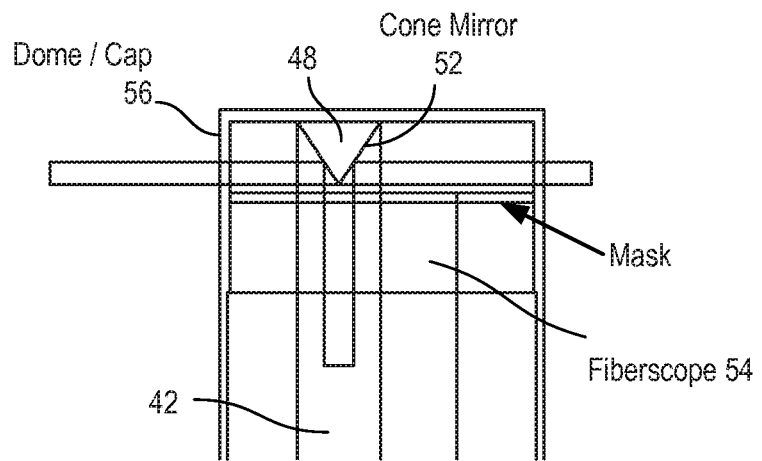

Referring to FIG. 3A, the distal end of the probe 34 is shown in cross section with the wide angle lens 14 positioned proximal to ends of the fiber scope 54 and light conductor 42 carrying the laser light. The wide angle lens defines a field of view 46 as shown by the dotted lines. Extending back proximally from the lens is one of the image conductors 44 configured to carry the images or data on the partial lateral portion(s) 20. Notably, the field of view of the illustrated embodiment is a full 150 degrees wherein the light pattern 16 may extend laterally out at right angles to the optical axis of the wide angle lens. Angles up to 180 degrees are possible but wider angles can be increasingly difficult to minimize distortion.

Extending under and past the wide angle lens 14 are the light conductor 42 and the distal end of the fiber scope 54 which includes a conductor(s) (such as a fiber optic bundle) for diffuse light and return conductor(s) for returning navigation images. At the distal most tip of the light source 12 is positioned the mirror 52 having a conical shape and configured to redirect the laser light into the pattern 16. If the conical shape is more or less than a 45 degree angle with respect to the axis of the laser light, the shape of the pattern 16 a conical surface. At 45 degrees, the shape is the planar surface 60 shown in FIG. 2.

Figure 3D:
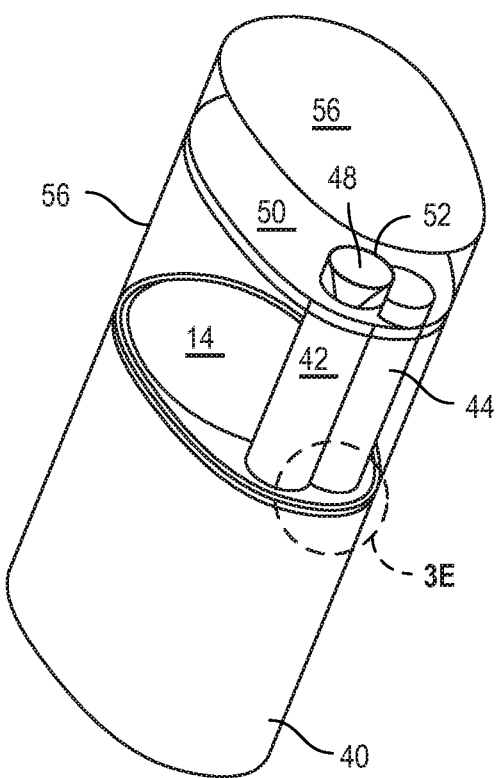
Figure 3E:
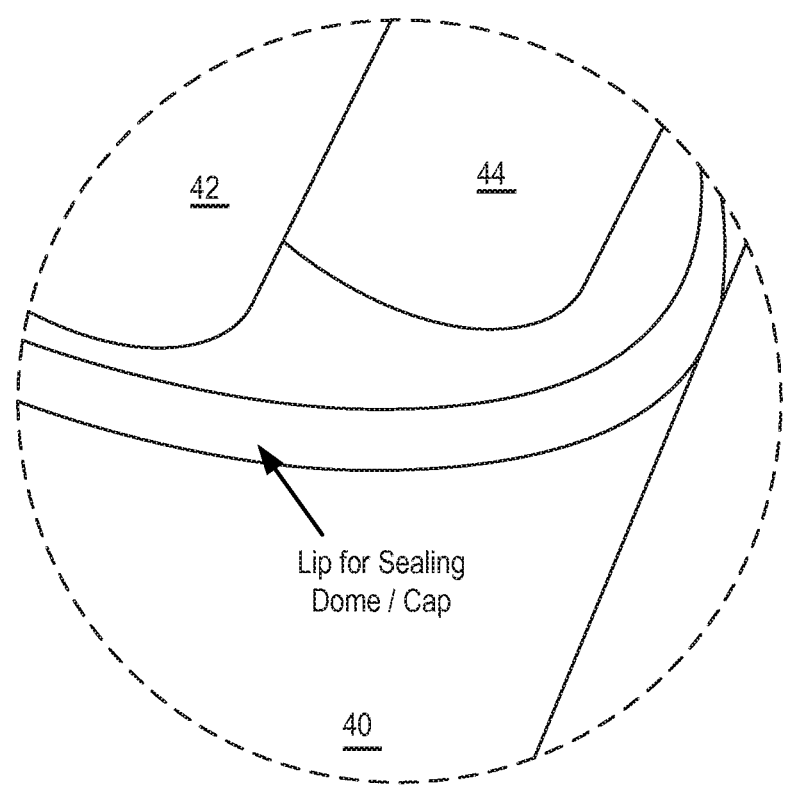

The mask 50 is a planar sheet with a pair of holes, as shown in FIG. 3D, and is preferably constructed of a transparent material to block reflections from the redirected laser light back to the wide angle lens 14 that may not be representative of the surface being detected and measured. The holes allow for passage of the light conductor 42 transmitting the laser light to the cone mirror 52 and the image conductor 44 for the fiber scope 54.

The transparent side walls 58 and the cap 56 are configured to enclose and protect the distal portions of the probe 34 but at the same time allow passage of the laser light pattern 16, diffuse navigation light from the fiber scope 54 and the images resulting and returning therefrom. The cap 56 may be, but does not need to be, transparent for the fiberscope. Optionally, as shown in FIG. 3, an opening in the cap 56 may allow passage and/or viewing by the fiberscope.

Because the light conductor 42 and the image conductor extend distal to the wide angle lens 14, the images of the projected pattern 16 of light as it strikes a surface are not completely detected and returned through the full 360 degree field. Instead, in a roughly cylindrical opening such as the ear canal, the returned partial lateral portion 20 may only be a "C shape" that leaves out a portion blocked from visibility by the light conductor 42 and image conductor 44.

Figure 4:
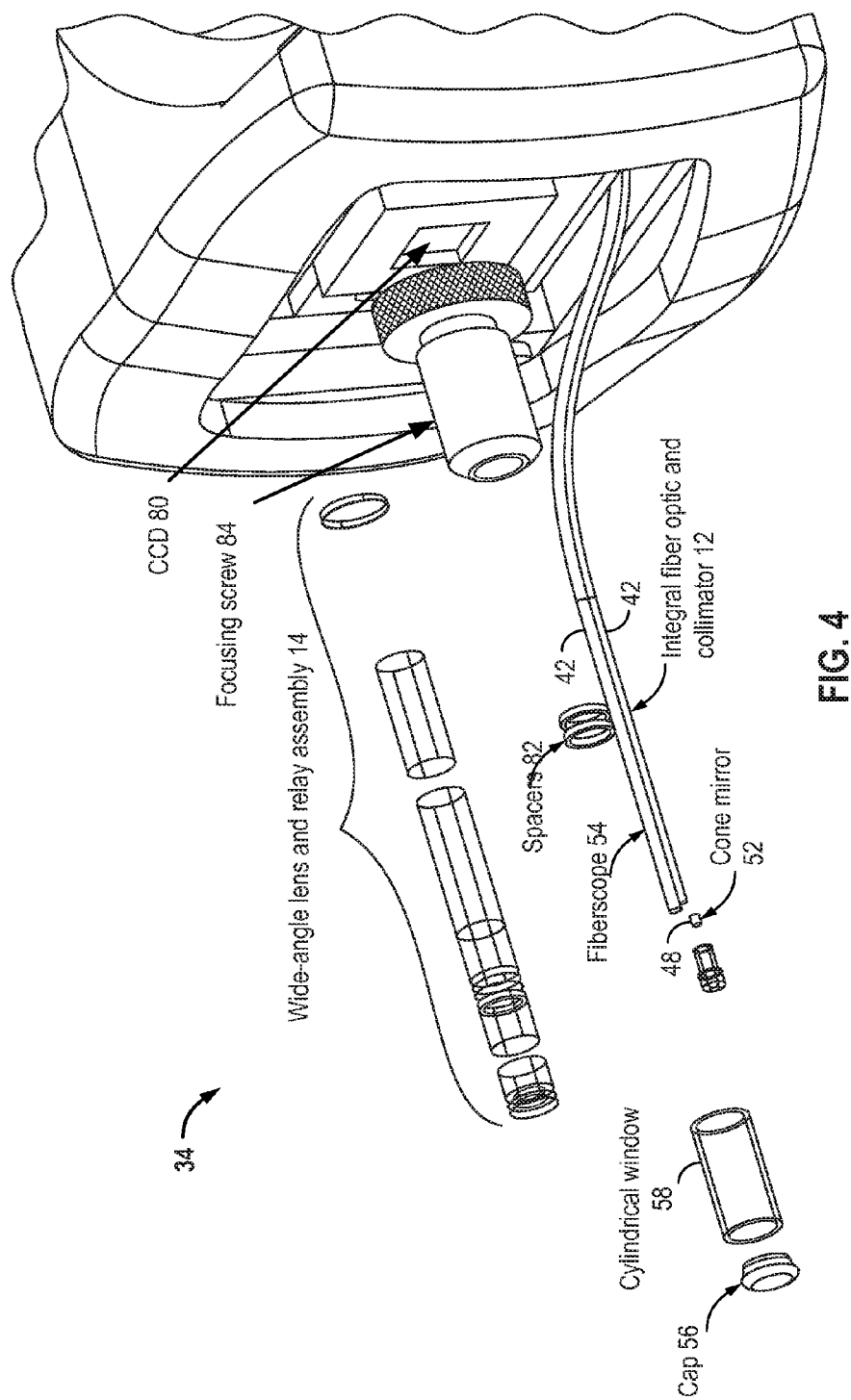
FIG. 4 is an exploded view of the probe of FIG. 2.

FIG. 4 shows an exploded view of a probe 34 of another embodiment of the present invention with the outer shaft 40 removed to better illustrate the function of the optical components. Starting distally, the cap 56 is assembled to the transparent side walls 58 which are formed by a short section of transparent cylindrical tube. Also distal is the mirror 52 which is mounted in a mirror tube and affixed to the end of laser light conductor 42. The laser light conductor 42 may also include a collimator function to generate a collimated beam for redirection into the pattern 16 by the cone mirror 52.

The fiberscope 54 has its distal end near the cone mirror 52 and extends proximally in a path adjacent to the light conductor 42 within the shaft 40. Both the fiber scope 54 and the light conductor 52 bend around a CCD camera chip 80 and into the body of the probe 34 to pass through the cable 76 to the computer system 68.

Also within the shaft 40 of the probe 34, the wide angle lens 14 and its image conductor 44 extend back from the cylindrical window 58 in a generally parallel relationship to the conductors 42, 44. The relative positioning of the optical components of the wide angle lens 14 is maintained in part by use of a pair of spacers 82. The wide angle lens 14 is a plurality of optical lens elements that include the image conductor 14 returning the image of the lateral portions 20 to the CCD camera chip 80 mounted in the body of the probe as shown in FIG. 4.

Supporting the wide angle lens 14 is a focusing screw 84 that when turned adjusts the focus of the wide angle lens 14, thereby changing the position of its focal surface for improved accuracy within different body orifices and for compensating for manufacturing tolerances and for improved accuracy within a variety of orifices. Proximal to the focusing screw 84 is the CCD camera chip that receives the images of the lateral portions 20 and converts those images into pixel data for return to the computer 68 for processing.

The term "wide angle lens" as used herein means any lens configured for a relatively wide field of view that will work in tortuous openings such as the ear canal 70. For example, for an ear canal, a 63 degree angle results in a lens-focal surface offset about equal to the maximum diameter of the ear canal that can be scanned with a centered probe 34. Notably, the focal surface of a 60 degree lens (a fairly standard sized wide angle lens) is equal to the diameter, resulting in a forward focal surface of about 6 mm, which is short enough to survive the second bend in an ear canal which is at about a 6 mm diameter. Therefore, for the purpose of ear canals, wide angle lenses are 60 degrees or greater. Other increments that work even better are 90 degrees with its 2:1 ratio allowing a forward focal surface distance of about 3 mm, allowing the probe 34 to be fairly short. Lenses that are greater than 90 degrees are possible as are lenses that include complex optical elements with sideways only views and no forward field of view.

Figure 5:
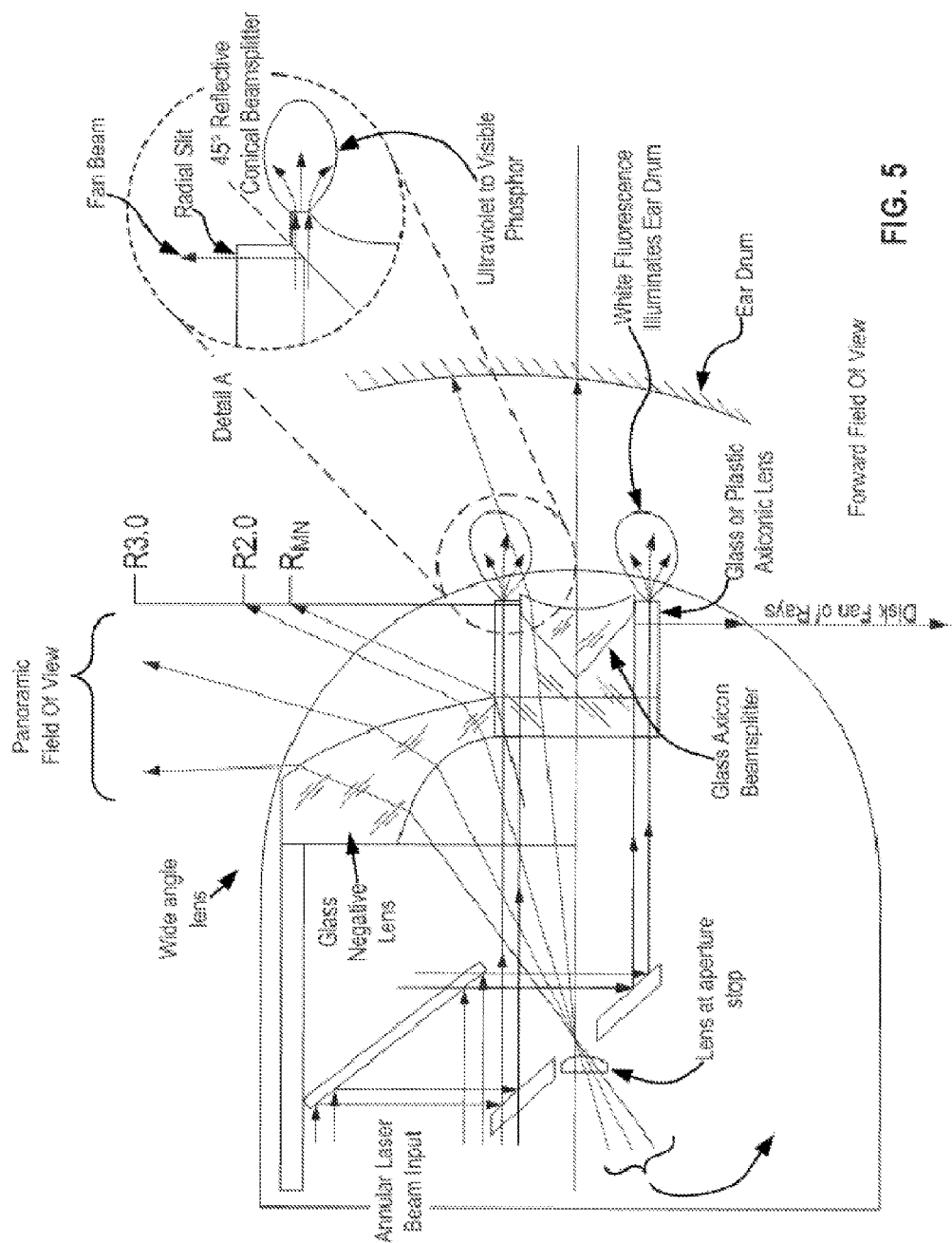
FIG. 5 is a schematic of another embodiment of the present invention using a beam splitter in the forward field-of-view of the wide angle lens.

In another embodiment, illustrated FIG. 5, the device 10 may not need a fiber scope 54 and instead the wide angle lens 14 is used for the forward field of view. A beam splitter diverts the center of the wide angle lens field to a second camera that is focused further in front of the probe 34 and is configured to image the forward (nonlaser-lit) view. A diffuse light source may be provided to illuminate ahead of the probe 34.

Figure 6:
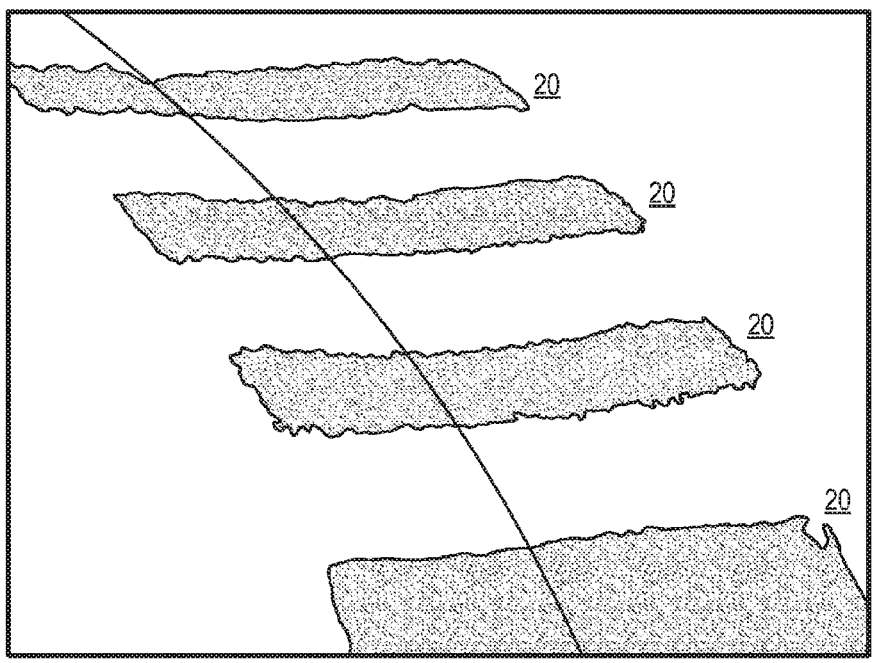
FIG. 6 is an image of a skin target illuminated by a laser light pattern for calibration.
Figure 7:
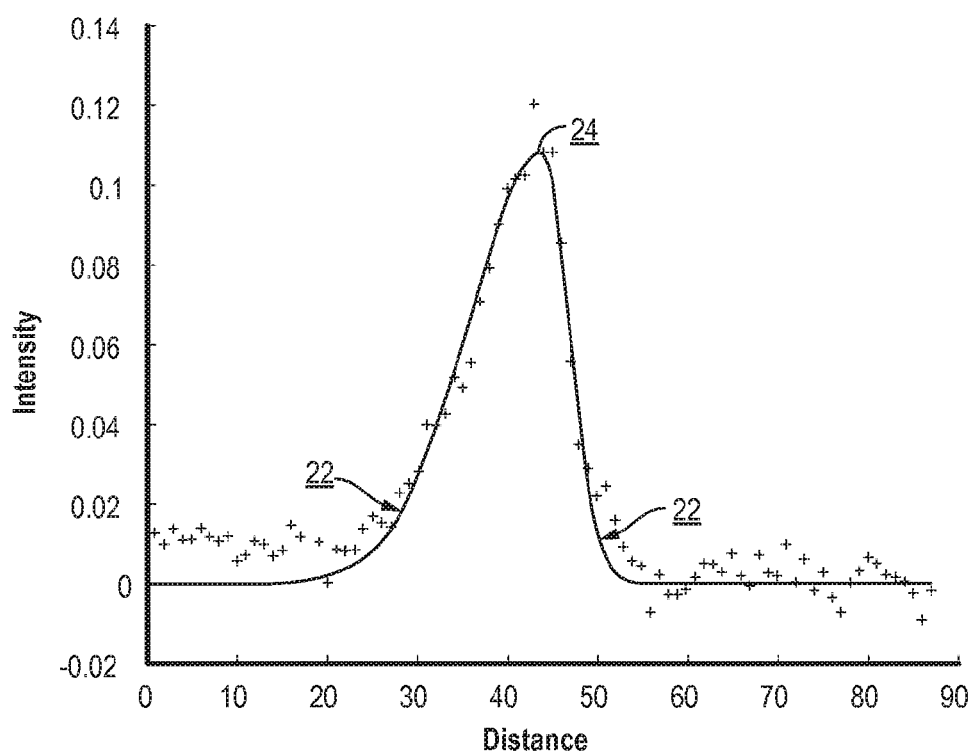
FIG. 7 is a cross-section of a thickness of a lateral portion of the laser light pattern of FIG. 6 showing an intensity distribution across the thickness.

Referring to FIG. 6, a skin target is shown with partial lateral portions 20 of the pattern 16 projected thereon for the purpose of determining how the laser pattern 16 will project upon skin and its location be marked. A perpendicular section of one of the lateral portions, as shown in FIG. 7, shows that the light intensity (y-axis) varies in a bell-curve shape with the thickness (x-axis) of the section. Thus, the partial lateral portion 20 may include an edge 22 of the light pattern 16 or a ridge 24 of the light pattern. These landmarks may be used to determine the position of the lateral portion 20 in the coordinate system. For example, one of the aforementioned landmarks could be found (such as by a ridge detecting function of the processor 26) or an inside edge of the lateral portion or an outside edge of the lateral portion. Or, an average of the inside and outside portions may be used.

An advantage of the present invention is that the wide angle lens 14 can view relatively proximate lateral portions of the body surface with high precision due to overlap of its focal surface with the pattern 16 of laser light. The term "focal surface" as used herein refers to a thickness within a range of focus of the wide angle lens 14 that is capable of achieving a certain base line resolution, such as being able to discern a 50 micrometer feature or smaller. For example, lateral positioning of the pattern 16 within the focal surface allows one pixel to be equivalent to about 50 micrometers. The focal surface itself has a bell curve distribution of resolution that allows variations in overlap or thickness of the focal surface and the width of the lateral portion 20 which, as shown above, has its own curved distribution across its thickness.

Generally, the wide angle lens 14 should have a reasonably low distortion threshold to meet the resolution goals. Most wide angle lenses can be as high as −80 percent or −60 percent distortion that would need to be compensated by improved accuracy in other areas such as placement of the focal surface and lateral portion 20. Therefore, there is no set threshold although collectively the various components are preferably tuned to allow a 50 micrometer or better resolution for lateral distances from the optical axis of the wide angle lens 14. The inventors have found that a distortion of better than −40 percent works well with preferred fields of view mentioned herein for ear canal applications.

The tracker or tracking system 28 is configured to determine a position of the probe 34 in the coordinate system and the body 30 of the patient in the coordinate system. The processor 26 is configured to use this information to determine the position of the probe 34 and its measurements relative to the body 30. The tracking system 28 may include elements of a commercially available tracking system such as the POLARIS SPECTRA from NDI of Waterloo, Ontario, Canada. The system is a two camera system to allow three-dimensional position determination of objects in its field of view including the patient and the probe 34 through the probe markers 36 and the body markers 38.

Once the field of view is calibrated to establish the coordinate system the probe 34 and its laser pattern 16 are calibrated using a target placed in the field of view. For such calibration, it is assumed that the laser pattern 16 and the optics, including the wide angle lens 14, are perfect and that the probe 34 is rigid. This enables referencing of the laser pattern 16 directed to the coordinate system.

Figure 8:
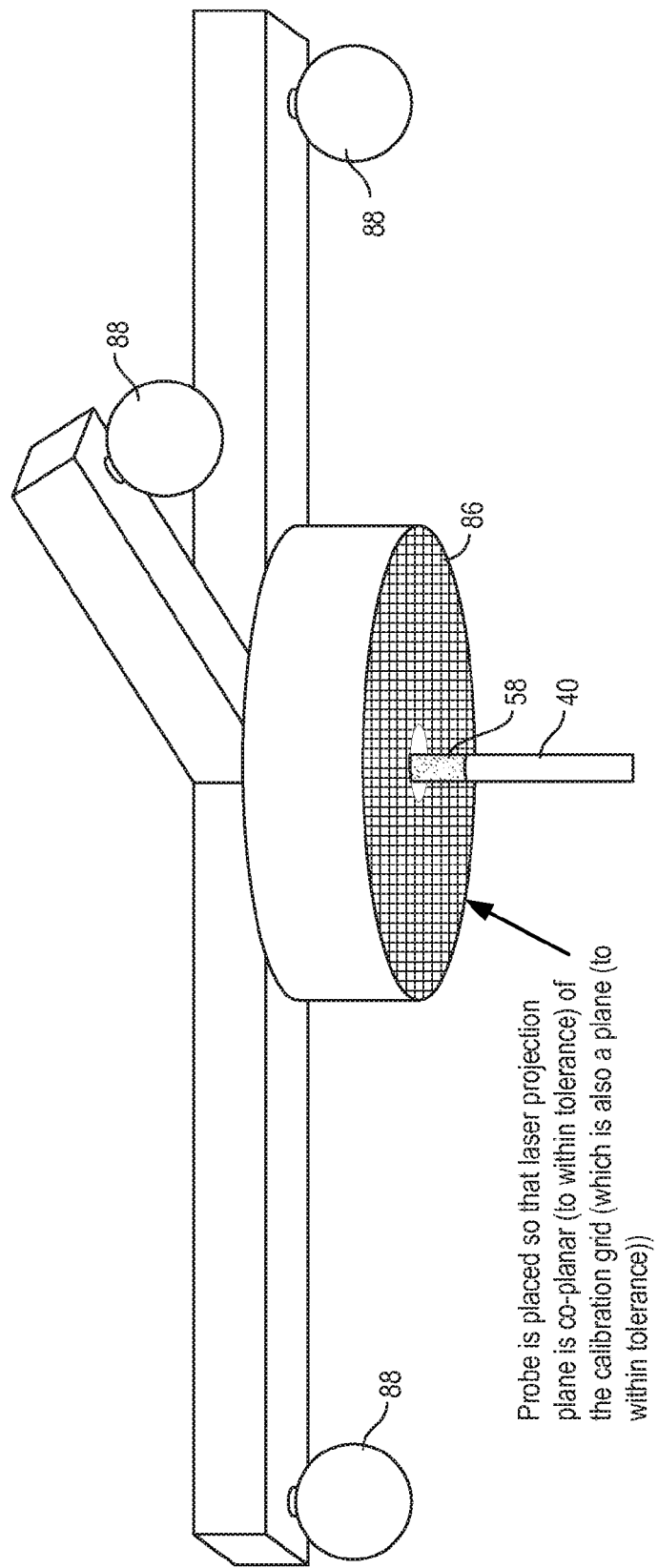
FIG. 8 is a target used for calibration of the probe of FIG. 2.

As shown in FIG. 8, for example, the target includes a checkerboard 86 connected to a pair of optical markers 88 carefully aligned with the z-axis of the probe 34. The relative location of 86 with respect to 88 is known by performing photogrammetry on the calibration object. In particular, the probe 34 is placed so that the projected laser pattern 16 is co-planar (to within tolerance) with the calibration grid (to within tolerance). This may be aided by a hole in the target that allows passage of the probe 34. Positioning is established when the laser light pattern 16 smears across the surface of the target 86.

With the checkerboard 86 in place, a tracking session is performed with the tracker 28 to establish the position of the checkerboard with the markers 88 and the position of the probe with the probe markers 36. Then, while maintaining the relative relationship of the probe 34 and the checkerboard 86, a lamp or light is shined on the checkerboard 86 and an image of it is collected through the wide angle lens 14. Preferably, the direction of the y-axis and z-axis relative to the tracker 28 is also noted to avoid axial direction errors.

Calibration may also include non-planar light patterns wherein a checkerboard is exposed to the light pattern in several different orientations. The intersection of the light pattern lateral portion with the checkerboard lines allows a reconstruction of the shape of the non-planar light pattern with respect to the wide-angle lens. Using a target similar to that illustrated in FIG. 8, it is possible to relate the reconstructed shape of the pattern into the coordinate system of the handheld.

Figure 9:
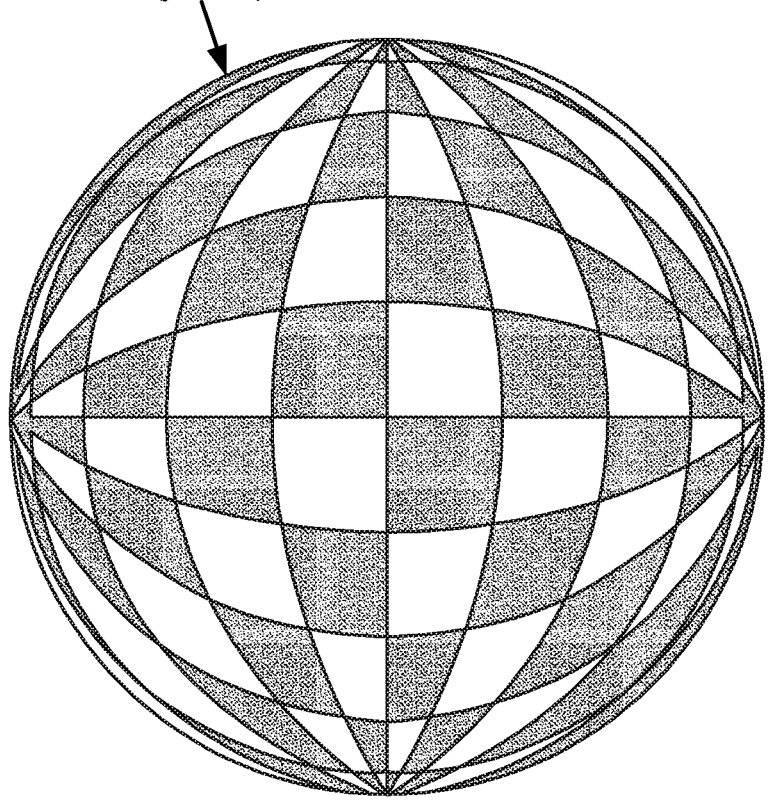
FIG. 9 is a simulated image of the target of FIG. 8 captured using a wide angle lens of the probe of FIG. 2.

FIG. 9 shows the simulation of the calibration image. The distance from the optical markers 88 to each of the corners of the checkerboard 86 and the laser pattern 16 is coincident with the corners of grid points on the checkerboards. Thus, the three dimensional position of the laser hitting the surface may be interpolating to determine the nearest grid point of the checkerboard 86. This information is then used fix the laser pattern within the coordinate system.

Figure 10:
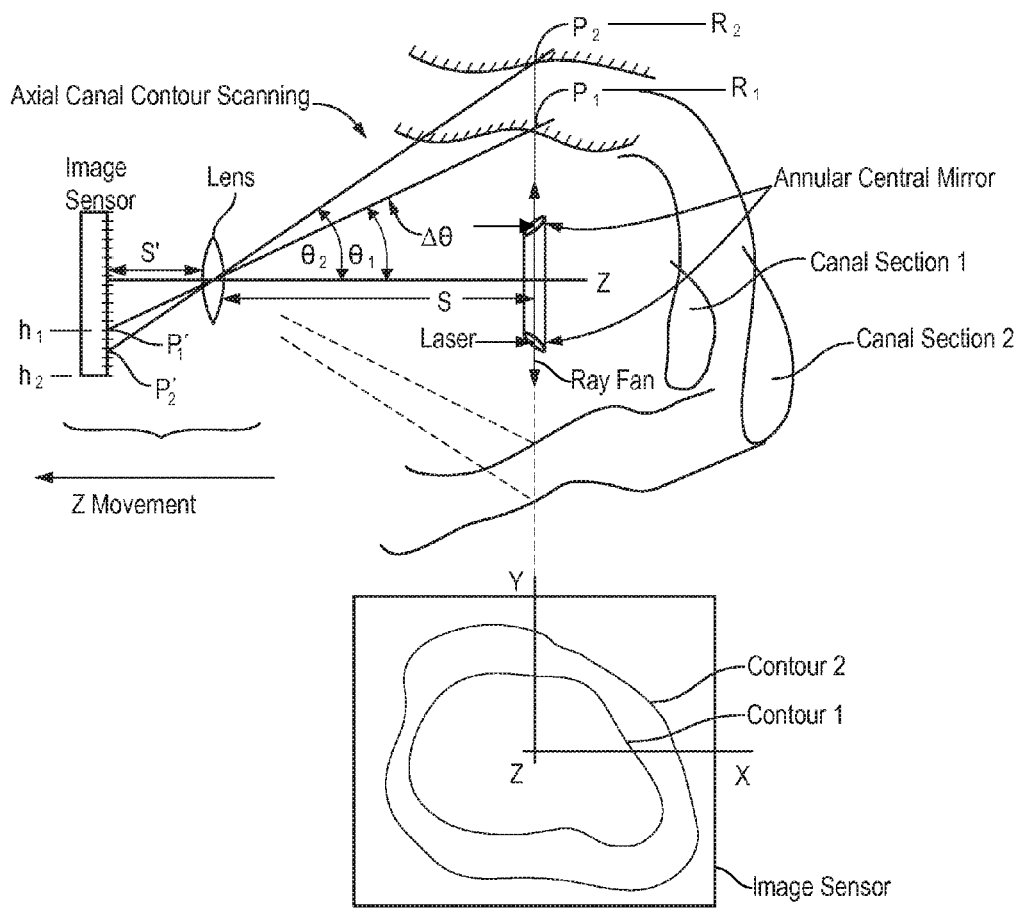
FIG. 10 is a schematic of the mathematics and geometry used by a processor to detect a radial distance or position of the lateral portions of the laser light pattern intersecting a measured surface.

In another embodiment, the device 10 includes a processor 26 that's connected in communication with the wide angle lens 14 and is configured to perform several functions including: determining a position of the lateral portion 20 in the coordinate system determining the position of the lateral portion 20 using a known focal surface determining the position of a plurality of the lateral portions 20 in the coordinate system and a corresponding location of the coordinate system relative to the body 30 combining the lateral portions 20 together into a three-dimensional shape 32 of a body orifice (such as an ear canal) using the positions and the corresponding locations FIG. 10 schematically shows an embodiment for calculation of the radial distance of the lateral portion 20 from the optical axis of the probe 34 as implemented by the processor 26. The position can be determined by triangulation, as shown in equations 1-7.

$$\frac{h}{S'} \equiv \frac{R}{S} \quad \text{Equation 2}$$

$$R = \frac{hS}{S'} \quad \text{Equation 3}$$

$$\frac{dy}{dx} = \frac{S'}{S} = M \quad \text{Equation 4}$$

$$R = \frac{h}{M} \quad \text{Equation 5}$$

$$\Delta R = \frac{\Delta h}{M} \quad \text{Equation 6}$$

$$\theta_{min} = \text{Tan}^{-1}\left(\frac{R_{min}}{S}\right) \quad \text{Equation 7}$$

$$\theta_{max} = \text{Tan}^{-1}\left(\frac{R_{max}}{S}\right) \quad \text{Equation 8}$$

In the example of FIG. 10 and in equations 1-7, a coordinate system for the scanner is oriented so that its Z axis is centered and fixed as the central axis of a scanning probe, looking end-on into the probe, here also referred to as the imaging axis. In this example, therefore, the ratio of the distance R from the imaging axis of a laser-illuminated point to the distance S between the laser plane and the lens is equal to that of the distance h from the center of the image sensor to the distance S' between the image sensor surface and the lens. Magnification M is the ratio of S' and S. When the distances S and S' between the lens and laser plane, and lens to image sensor are known, equations 1-7 can reconstruct the geometry of illuminated points in the coordinate system. These equations also denote that for a focal surface such as a plane, there is a 1:1 mapping of points in the coordinate system to pixel locations on the image sensor.

The image sensor may be implemented in complementary-symmetry metallic-oxide-semiconductor ('CMOS') sensor, as a charge-coupled device ('CCD'), or with other sensing technology as may occur to those of skill in the art. A CMOS sensor can be operated in a snapshot readout mode or with a rolling shutter when the scan along the Z-axis is incremented or stepped synchronously to effect a readout of a complete frame. Similar incrementing or stepping may be used for a CCD operated with interlacing scans of image frames.

Figure 11:
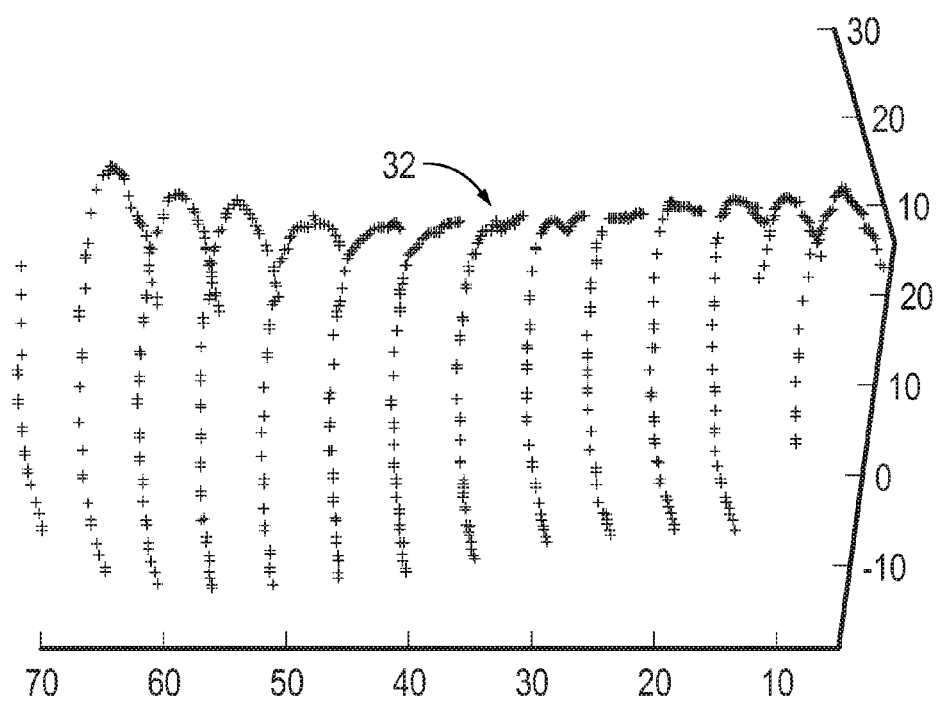
FIG. 11 is a three-dimensional shape of a portion of an ear canal reconstructed by a computer shown in FIG. 1.

FIG. 11 shows an exemplary three-dimensional shape 32 of an ear canal 92 constructed from a plurality of the lateral portions assembled using the processor 26.

Figure 12:
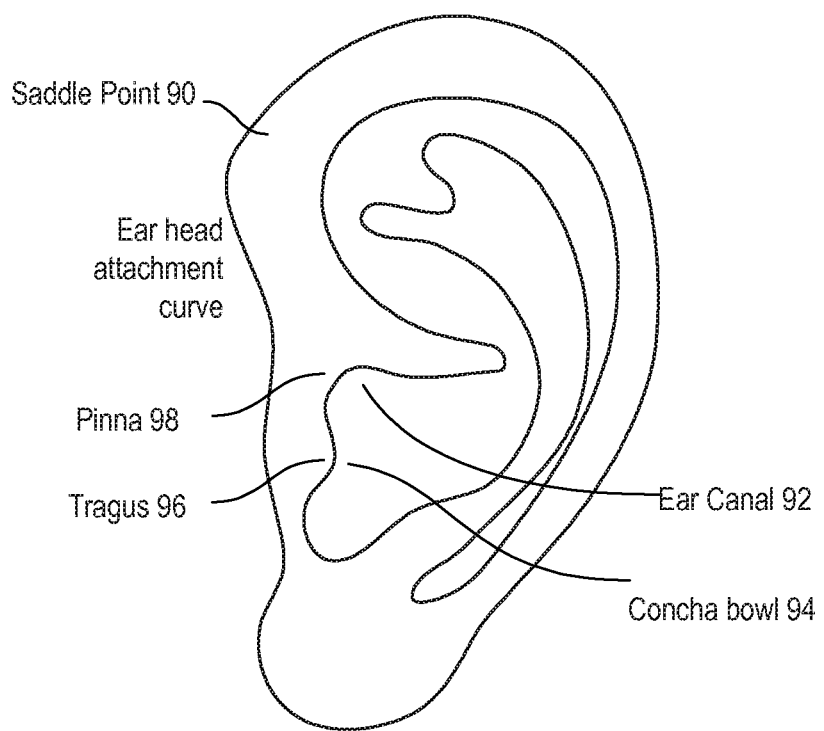
FIG. 12 is a perspective view of ear anatomy used in a method for measuring a geometry of an ear saddle of another embodiment of the present invention.

In another embodiment of the present invention, as shown in FIG. 12, the device 10 may be used to measure anatomical features well-suited to facilitate creation of a hearing aid. These features include a saddle 90, ear canal 92 and concha bowl 94. The ear canal 92 and concha bowl 94 are scanned as described above and the probe 34 is rotated so the laser pattern 16 falls upon the surface of the outside of the tragus 96. The scan moves up the pinna 98 until the saddle point 100 is reached and the scan progresses 10 to 15 mm beyond the saddle point 100. This data is transmitted to the processor 26, along with the orifice data, to construct the three-dimensional shape 32 used to custom build the hearing aid.

Figure 13:
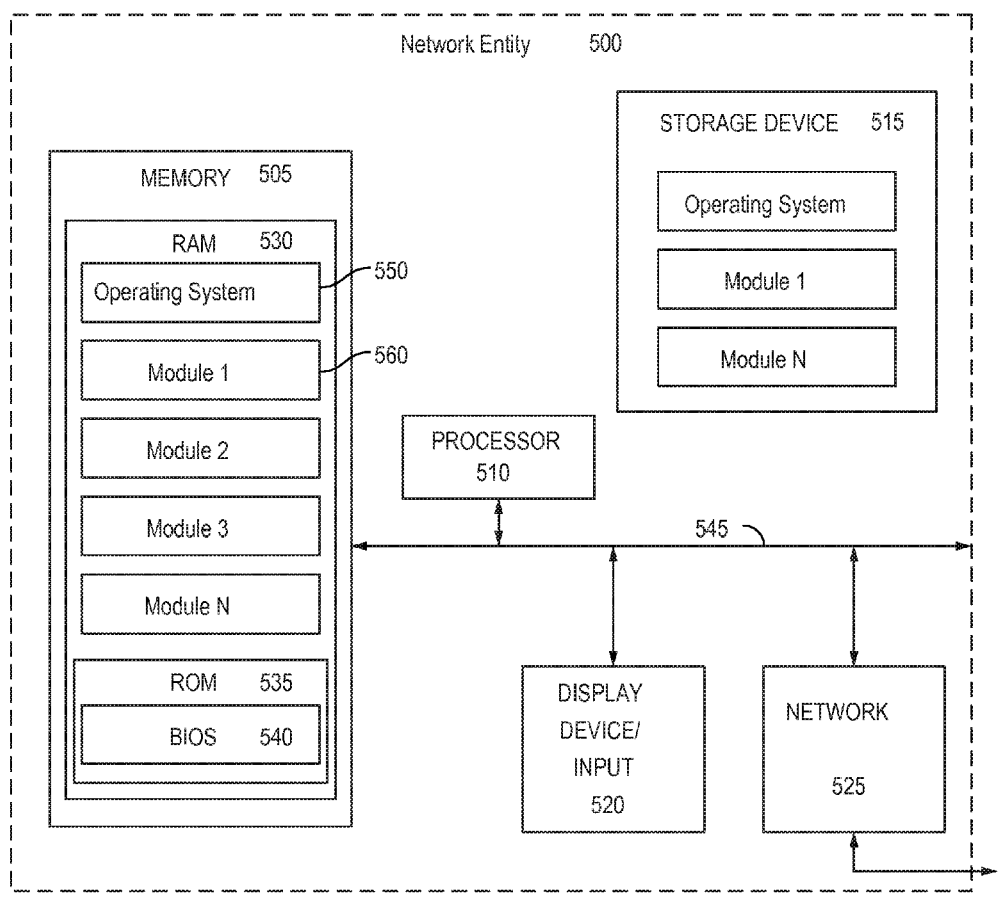
FIG. 13 is a schematic of a computer system of another embodiment of the present invention for optically determining surface geometries.

Referring now to FIG. 13, a schematic diagram of a central server 500, or similar network entity such as the computer 68 shown in FIG. 1, configured to implement a system for measuring body surfaces according to one embodiment of the invention, is provided. As used herein, the designation "central" merely serves to describe the common functionality the server provides for multiple clients or other computing devices and does not require or infer any centralized positioning of the server relative to other computing devices. As may be understood from FIG. 13, in this embodiment, the central server 500 may include a processor 510 (such as the processor 26) that communicates with other elements within the central server 500 via a system interface or bus 545. Also included in the central server 500 may be a display device/input device 520 for receiving and displaying data. This display device/input device 520 may be, for example, a keyboard or pointing device that is used in combination with a monitor, or the CCD 80 or the tracker 28 shown in FIGS. 1 and 4. The central server 500 may further include memory 505, which may include both read only memory (ROM) 535 and random access memory (RAM) 530. The server's ROM 535 may be used to store a basic input/output system 540 (BIOS), containing the basic routines that help to transfer information across the one or more networks.

In addition, the central server 500 may include at least one storage device 515, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 515 may be connected to the system bus 545 by an appropriate interface. The storage devices 515 and their associated computer-readable media may provide non-volatile storage for a central server. It is important to note that the computer-readable media described above could be replaced by any other type of computer-readable media known in the art. Such media include, for example, magnetic cassettes, flash memory cards and digital video disks.

A number of program modules may be stored by the various storage devices and within RAM 530. Such program modules may include an operating system 550 and a plurality of one or more (N) modules 560. The modules 560 may control certain aspects of the operation of the central server 500, with the assistance of the processor 510 and the operating system 550. For example, the modules may perform the functions described above and illustrated by the figures and other materials disclosed herein.

The schematics, flowcharts, and block diagrams in the FIGS. 1-13 illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Advantages of the embodiments of the invention described herein include the relatively short distance (3 mm, 2 mm, 1 mm or less) of the pattern 16 and focal surface 18 extending past the probe 34 that allow it to image laterally in orifices with tortuous geometry, such as ear canals with a small diameter and where it is useful to scan 3 mm past a bend and also to image larger diameter ear canals and spaces without having to take multiple passes over that section of the canal. Also, the low distortion of the wide angle lens 14 leads to high resolution when the laser pattern 16 is coincident with the focal surface 18. This allows the resolution of 50 micrometers for a single pixel when other prior art systems have neighboring pixels a millimeter or more apart.

Advantages particular to the creation of hearing aids include a solution that allows directly scanning of the ear instead of making a silicone mold. Quality, performance and fit are improved while reducing cost and increasing speed of production by capturing the shape and size of the ear canal for submission directly to the hearing aid manufacturer. Other medical applications include endoscopic surgery, dental impressions and the aforementioned industrial applications, such as inspection of various pipes, channels, tubing or other openings.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. For example, a camera may be any kind of image sensor. The embodiment was chosen and described in order to best explain the principles of the invention and the practical application, and to enable others of ordinary skill in the art to understand the invention for various embodiments with various modifications as are suited to the particular use contemplated.

What is claimed is:

1. Apparatus for scanning a three dimensional ('3D') object, the apparatus comprising:
   a otoscanner body having mounted upon it a scanning probe, the scanning probe comprising a laser light source, a laser optical element, a source of non-laser video illumination, a wide-angle lens optically coupled to an image sensor, and an image sensor mounted within the otoscanner body and coupled for data communications to a data processor;
   a plurality of tracking illumination sensors, the tracking illumination sensors sensing reflections of tracking illumination emitted from a tracking illumination emitter and reflected from tracking fiducials installed at positions that are fixed relative to the scanned object, the tracking illumination sensors also sensing reflections of tracking illumination emitted from the tracking illumination emitter and reflected from tracking targets installed at fixed positions on the otoscanner body; and
   the data processor configured so that it functions by constructing, in dependence upon a sequence of images captured when a scanned object is illuminated by laser light and tracked positions of the scanning probe inferred from reflections of tracking illumination sensed by the tracking illumination sensors, a 3D image of the scanned object.

2. The apparatus of claim 1 further comprising a display screen coupled for data communications to the image sensor, the display screen displaying images of the scanned object.

3. The apparatus of claim 2 wherein the display screen displaying images of the scanned object further comprises the display screen displaying video images from the image sensor of the scanned object illuminated only by non-laser video illumination.

4. The apparatus of claim 2 wherein the display screen displaying images of the scanned object further comprises the display screen displaying the 3D image of the scanned object.

5. The apparatus of claim 1 further comprising a display screen coupled for data communications to the image sensor, the display screen displaying images of the scanned object, the display screen mounted on the otoscanner body.

6. The apparatus of claim 1 wherein the laser light source in the scanning probe comprises an optical fiber that conducts laser light to the scanning probe from a laser outside the probe.

7. The apparatus of claim 1 wherein:
   the laser optical element comprises a conical laser-reflective optical element; and
   the laser light source and the conical laser-reflecting optical element are configured so that the conical laser-reflecting optical element, when illuminated by the laser light source, projects a broken ring of laser light upon an interior surface of the ear when the ear probe is positioned in the ear.

8. The apparatus of claim 1 wherein:
   the laser optical element comprises a laser optic lens; and
   the laser light source and the laser optic lens are configured so that the laser optic lens, when illuminated by the laser light source, projects upon the object laser light from a front surface of the laser optic lens.

9. The apparatus of claim 1 wherein the wide angle lens has a sufficient depth of field so that an entire portion of a surface of the scanned object illuminated by laser light is in focus at the image sensor.

10. The apparatus of claim 1 wherein constructing a 3D image of the scanned object further comprises, for a sequence from the image sensor of 2D images of the scanned object taken when the scanned object is illuminated by laser light from the scanning probe:
- detecting ridge points for each 2D image, the detecting further comprising identifying a set of brightest pixels for each 2D image, each set depicting a pattern of laser light reflected from a surface of the scanned object;
- transforming, in dependence upon a predefined association between each pixel in the image sensor and corresponding points in scanner space, the ridge points to points in scanner space; and
- transforming, in dependence upon a relationship between an origin of a coordinate system defining scanner space and an origin of another coordinate system defining object space, the points in scanner space to points in object space.

11. The apparatus of claim 1 wherein constructing the 3D image further comprises constructing the 3D image in dependence upon a sequence of images captured by the image sensor as the probe is moved relative to the scanned object.

12. The apparatus of claim 1 wherein the scanned object is an ear.

13. The apparatus of claim 1 wherein the scanned object is an interior portion of an ear.

14. The apparatus of claim 1 further comprising the scanning probe configured to extend into an orifice of a human body.

15. The apparatus of claim 1 wherein the laser light source comprises an optical fiber that extends further distally than the wide angle lens and into a field of view of the wide angle lens.

16. Apparatus for scanning a three dimensional ('3D') object, the apparatus comprising:
- an otoscanner body having mounted upon it a scanning probe, the scanning probe comprising an imaging light source, an imaging optical element, a wide-angle lens optically coupled to an image sensor, and an image sensor mounted within the otoscanner body and coupled for data communications to a data processor;
- a plurality of tracking illumination sensors, the tracking illumination sensors sensing reflections of tracking illumination emitted from a tracking illumination emitter and reflected from tracking fiducials installed at positions that are fixed relative to the scanned object, the tracking illumination sensors also sensing reflections of tracking illumination emitted from the tracking illumination emitter and reflected from tracking targets installed at fixed positions on the otoscanner body; and
- the data processor configured so that it functions by constructing, in dependence upon a sequence of images captured when a scanned object is illuminated by imaging light and tracked positions of the scanning probe inferred from reflections of tracking illumination sensed by the tracking illumination sensors, a 3D image of the scanned object.

17. The apparatus of claim 16 further comprising a source of video illumination and a display screen coupled for data communications to the image sensor, the display screen displaying images of the scanned object.

18. The apparatus of claim 17 wherein the display screen displaying images of the scanned object further comprises the display screen displaying video images from the image sensor of the scanned object illuminated only by video illumination.

19. The apparatus of claim 17 wherein the display screen displaying images of the scanned object further comprises the display screen displaying the 3D image of the scanned object.

20. The apparatus of claim 16 further comprising a display screen coupled for data communications to the image sensor, the display screen displaying images of the scanned object, the display screen mounted on the otoscanner body.

21. The apparatus of claim 16 wherein the imaging light source in the scanning probe comprises an optical fiber that conducts imaging light to the scanning probe from an imaging light source outside the probe.

22. The apparatus of claim 16 wherein:
- the imaging optical element comprises a conical reflective optical element; and
- the imaging light source and the conical reflecting optical element are configured so that the conical reflecting optical element, when illuminated by the imaging light source, projects a broken ring of imaging light upon an interior surface of the ear when the ear probe is positioned in the ear.

23. The apparatus of claim 16 wherein:
- the imaging optical element comprises an imaging optic lens; and
- the imaging light source and the imaging optic lens are configured so that the imaging optic lens, when illuminated by the imaging light source, projects upon the object imaging light from a front surface of the imaging optic lens.

24. The apparatus of claim 16 wherein the wide angle lens has a sufficient depth of field so that an entire portion of a surface of the scanned object illuminated by imaging light is in focus at the image sensor.

25. The apparatus of claim 16 wherein constructing a 3D image of the scanned object further comprises, for a sequence from the image sensor of 2D images of the scanned object taken when the scanned object is illuminated by imaging light from the scanning probe:
- detecting ridge points for each 2D image, the detecting further comprising identifying a set of brightest pixels for each 2D image, each set depicting a pattern of imaging light reflected from a surface of the scanned object;
- transforming, in dependence upon a predefined association between each pixel in the image sensor and corresponding points in scanner space, the ridge points to points in scanner space; and
- transforming, in dependence upon a relationship between an origin of a coordinate system defining scanner space and an origin of another coordinate system defining object space, the points in scanner space to points in object space.

26. The apparatus of claim 16 wherein constructing the 3D image further comprises constructing the 3D image in dependence upon a sequence of images captured by the image sensor as the probe is moved relative to the scanned object.

27. The apparatus of claim 16 wherein the scanned object is an ear.

28. The apparatus of claim 16 wherein the scanned object is an interior portion of an ear.

29. The apparatus of claim 16 further comprising the scanning probe configured to extend into an orifice of a human body.

30. The apparatus of claim 16 wherein the imaging light source comprises an optical fiber that extends further distally than the wide angle lens and into a field of view of the wide angle lens.

* * * * *